United States Patent [19]
Xie

[11] Patent Number: 4,768,023
[45] Date of Patent: Aug. 30, 1988

[54] DIAPER WETNESS SIGNALLING SYSTEM

[76] Inventor: Alex J. Xie, 89-24 120th St., Richmond Hill, N.Y. 11418

[21] Appl. No.: 25,186

[22] Filed: Mar. 12, 1987

[51] Int. Cl.$^4$ ............................................. G08B 23/00
[52] U.S. Cl. ................................ 340/573; 128/138 A
[58] Field of Search ............................. 340/573, 604; 128/138 A; 200/61.04–61.05

[56] References Cited

U.S. PATENT DOCUMENTS

| | | | |
|---|---|---|---|
| 4,106,001 | 8/1978 | Mahoney | 128/138 A X |
| 4,191,950 | 3/1980 | Levin et al. | 128/138 A X |
| 4,212,295 | 7/1980 | Snyder | 340/573 X |
| 4,356,818 | 11/1982 | Macias et al. | 128/138 A |
| 4,484,573 | 11/1984 | Yoo | 128/138 A |

Primary Examiner—Glen R. Swann, III
Assistant Examiner—Thomas J. Mullen, Jr.

[57] ABSTRACT

This invention consists, in part, of a disposable diaper containing a pair of embedded electrodes terminated by a pair of conductive and adhesive tapes on the outer surface of the diaper.

This invention additionally consists of a compact diaper wetness signalling device contained in a housing and comprised of a CMOS voltage comparator with a reference voltage set by a Zener diode and a resistor, a voltage divider, a beeper, and a battery. The device has a pair of conductive contacts fixed into recesses on the outer surface of the housing, and the device can be detachably adhered to the conductive adhesive tapes. When the diaper is wet, the resistance across the two electrodes embedded in the diaper decreases, and this resistance decrease offsets the input voltage of the comparator, causing the beeper to be turned on.

9 Claims, 3 Drawing Sheets

DIAPER WETNESS SIGNALLING SYSTEM

BACKGROUND OF THE INVENTION

For many years, a variety of designs has been developed for signalling wetness in a baby's diaper, but because of comfort and cost reasons, none of these designs has resulted in a successfully marketed product.

Prior inventions for signalling wetness in a baby's diaper include: U.S. Pat. Nos. 3,460,123; 3,759,246; 3,809,078; 4,106,001; 4,212,295; 4,356,818; 4,484,573; and 4,539,559. These inventions, as concerns comfort, easy of use, and economics, have a common weakness: namely, the method of connecting the designed device with the diaper. A way to rectify this weakness is one of the objects of the current invention.

SUMMARY OF THE INVENTION

This invention provides a disposable baby's diaper with a state of the art of electrical connection between the diaper and a detecting and signalling device.

The disposable diaper is comprised of an inner sheet, an absorbing sheet containing a pair of spaced thin wires as electrodes to sense the wetness, and an outer sheet. Said wires are embedded longitudinally in the diaper with one of their ends extending out through two apertures on the outer sheet and are terminated at outer surface of said outer sheet by a pair of spaced electrically conductive tapes coated with a conductive adhesive coating. A detachable backing sheet, coated with anti-adhesive material on both sides, covers the conductive tapes.

The device is contained in a two part housing, a top part and a bottom part, with a pair of conductive contacts fixed into the recesses on the outer surface of the bottom part of the housing. The circuit of the device is comprised of a CMOS voltage comparator with a reference voltage set by a Zener diode and a resistor, a voltage divider, a beeper with an oscillator and a driver which could be of the type found in a sound Christmas card, and a button type Lithium battery with a voltage which could be as low as 1.6 volts. The voltage divider is comprised of a resistor and a pair of conductive wires. When the diaper is wet, the pair of conductive wires will detect the lower resistance in the wet diaper and which causes the voltage on the voltage divider being moved across the reference voltage of the comparator which change the state of the comparator causing the beeper being turned on. When the diaper and device are been using the backing sheet will be peeled off and each one of the two conductive contacts on the surface of the housing are electrically connected to each one of the two electrodes in the diaper through the conductive adhesive tapes on the outer sheet of the diaper.

DESCRIPTION OF THE PREFERRED EMBODIMENT

Figure 1:
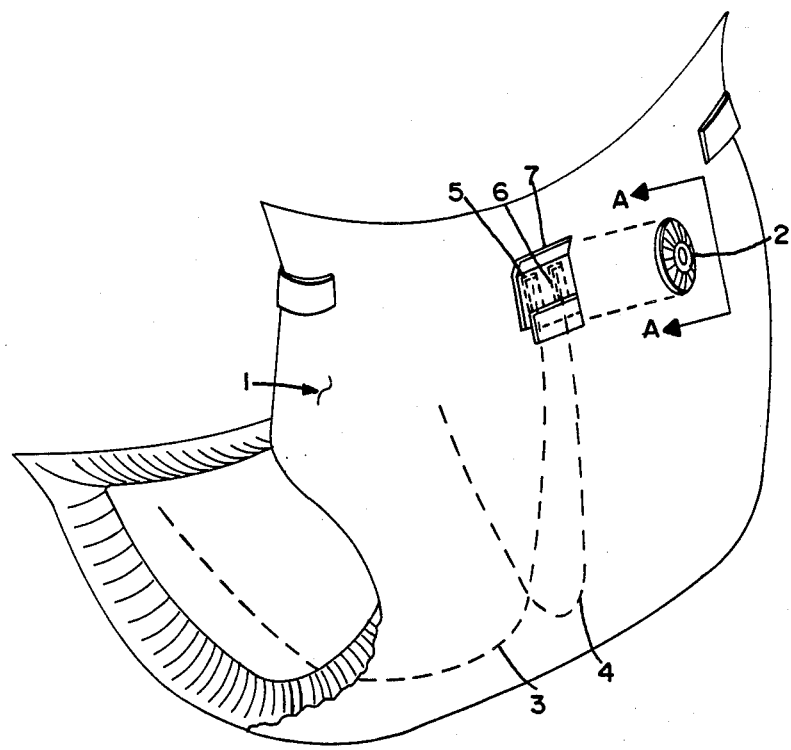
FIG. 1 is a perspective view of the currently invented diaper and device.

In the drawing of FIG. 1, the diaper 1, which is one of the subjects of this invention, can be used with the detecting and signalling device 2 which is another subject of this invention.

Figure 2:
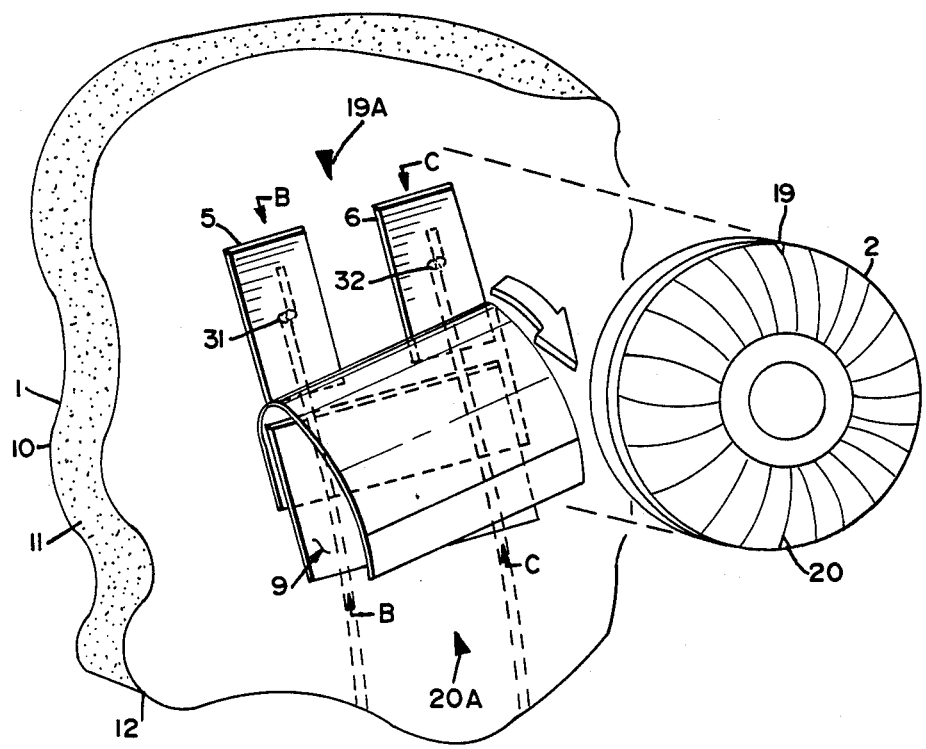
FIG. 2 is an enlarged perspective view of the device and the connection area of the diaper taken along the line A—A of FIG. 1.
Figure 3:
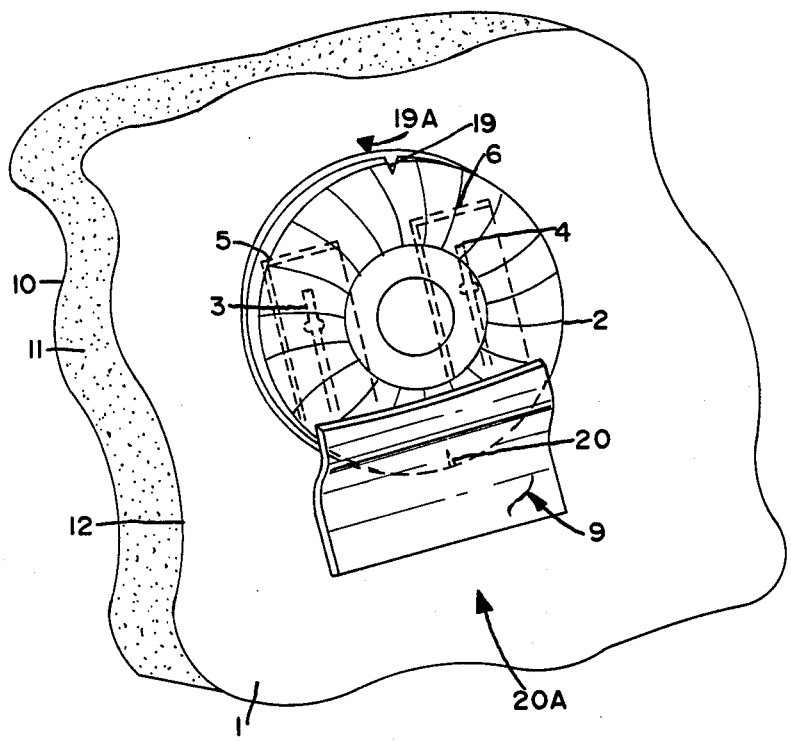
FIG. 3 is an enlarged perspective view of the connection area of the diaper, with the device attached to the diaper.
Figure 4:
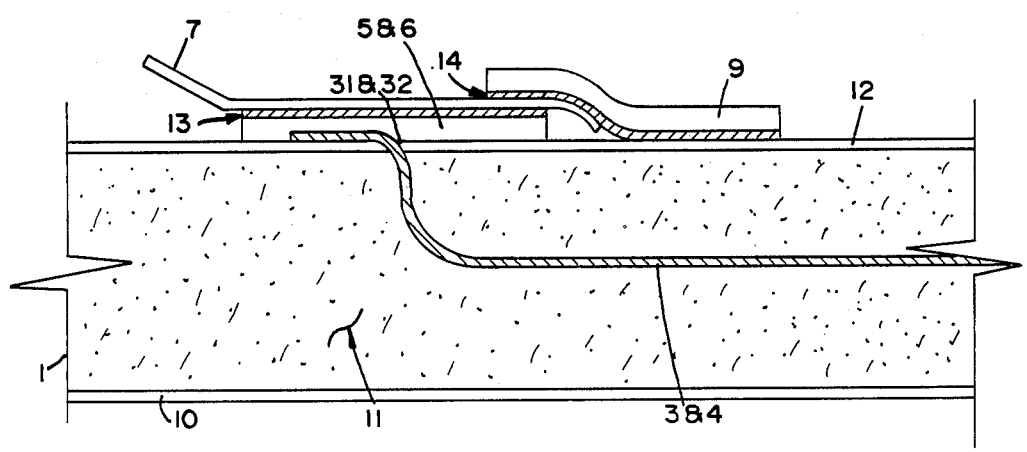
FIG. 4 is a sectional view of FIG. 2 taken along the line B—B or line C—C.

Referring to FIGS. 2, 3, and 4, the diaper 1 is comprised of an inner sheet 10 which allows baby's urine to pass through, an absorbing sheet 11 which absorbs the baby's urine, an outer sheet 12 which is made of waterproof material, a pair of spaced electrodes 3 and 4 made of a conductive fine wire, and a pair of spaced conductive tapes 5 and 6 coated with a conductive adhesive coating 13. The spaced electrodes 3 and 4 are embedded longitudinally in the absorbing sheet 11, with one end of each of said electrodes 3 and 4 extending out through each one of two apertures 31 and 32 on the outer sheet 12 to be electrically connected to the spaced conductive tapes 5 and 6, respectively. Each one of the conductive tapes 5 and 6 are pressed on to the outer surface of the outer sheet 12 by means of heat and/or conductive adhesive to make electrical contact with each one of the electrodes 3 and 4, respectively. A detachable backing sheet 7, coated with anti-adhesive material on both sides, covers the conductive adhesive coating 13 of the pair of the conductive tape 5 and 6. The backing sheet 7 will be peeled off when the diaper 1 and device 2 are being used. To more tightly hold the device 2 in place, a supporting sheet 9 coated with an adhesive coating 14, half of which adheres to the outer surface of the outer sheet 12 while the other half adheres to the backing sheet 7, could optionally be used.

Figure 6:
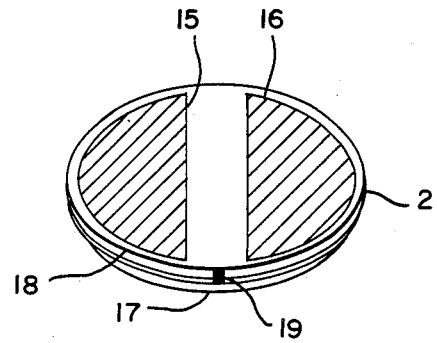
FIG. 6 is a perspective view of the device.

As shown in FIG. 6, the device 2 is comprised of a top housing 17 and a bottom housing 18. The top housing 17 and bottom housing 18 are made in such way that they can be snapped together to close.

Figure 7:
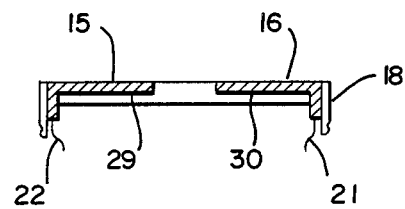
FIG. 7 is a sectional view of bottom part of the device.

Referring to FIG. 6 and 7, each one of the pins 21 and 22 is electrically connected to each one of the conductive contacts 15 and 16 which are fixed into the recesses 29 and 30, respectively, on the outer face of the bottom housing 18.

Figure 5:
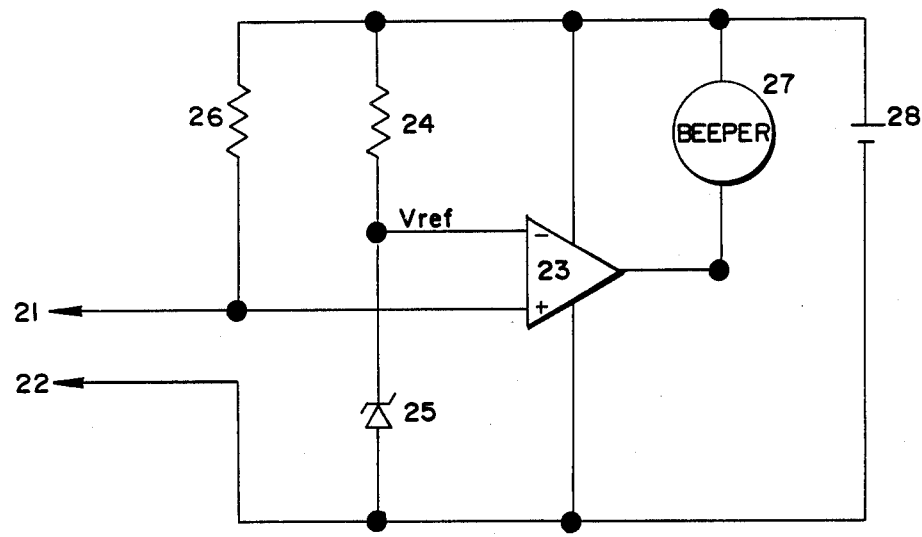
FIG. 5 is a schematic diagram of the device.

Referring to the schematic in FIG. 5, the electrical circuitry of the device 2 is comprised of a CMOS voltage comparator 23, a beeper 27 containing an oscillator and a driver, a button type Lithium battery 28. The reference voltage Vref of the comparator 23 is set by the Zener diode 25 and the resistor 24. The value of the resistor 26 can be selected as follows:

According to experiment, the resistance of soiled diaper is approximately 4 thousand ohms to 86 thousand ohms measured across one inch of soiled diaper, if we select the top value and add 50% of it as a contingency factor, we arrive at 129 thousand ohms. Vref can be set by the Zener diode 25 and the resistor 24. Assume the battery voltage is V. Then:

$$Vref = V*129/(129+R)$$

therefore the value of the resistor 26 is $129*(V-Vref)/Vref$ (thousand ohms).

When the diaper 1 is dry, the resistance across pin 21 and pin 22 is in the Mega-ohm range, so that the voltage on the input of the comparator 23 is much higher than Vref. Under this condition, therefore the output of the comparator 23 is high, and the beeper 27 is off.

Under wet conditions, the resistance across pin 21 and pin 22 is less then 86 thousand ohms, so that the voltage on the input of the comparator 23 is $V*86/(R+86)$, which is lower than Vref, therefore the output of the comparator 23 goes low, and the beeper 27 is turned on.

Referring to FIGS. 1, 2, 5 and 6, the device 2 is attached to the conductive adhesive tapes 5 and 6 to form a electrical loop through the conductive contact 15, the conductive adhesive tape 5, the electrode 3, the absorbing sheet 11, the electrode 4, the conductive adhesive tape 6, and the conductive contact 16, in sequence. To assist in properly aligning the conductive contacts 15 and 16 of the device 2 with respect to the pair of conductive adhesive tapes 5 and 6 on the diaper 1, alignment marks 19A and 20A may be printed on the outer surface of the outer sheet 12 of diaper 1, and corresponding alignment marks 19 and 20 may be incorporated into the device 2. When a diaper change is needed, said device 2 is removed from the wet diaper and attached to a fresh one.

While my above description contains many specifications, these should not be construed as limitations on the scope of the invention, but rather as an exemplification of one preferred embodiment thereof, many other variations are possible. For example: the terminals of the electrodes could be on the side of the diaper or in front of the diaper; the electrodes could be two groups of thin wires instead of two thin wires; the device supporting sheet could be a large one to cover whole device except the opening for releasing the alarm sound. Accordingly, the scope of the invention should be determined not by the embodiment illustrated, but by the appended claims and their legal equivalents.

I claim:

1. A disposable diaper adapted to detect and signal wetness, said diaper having an inner sheet, an absorbing sheet, and an outer sheet, and also including:
   (a) a pair of spaced electrodes embedded longitudinally in a major part of said diaper with one end of each one of said electrodes extending out through a respective one of two apertures on said outer sheet terminated on the outer surface of said outer sheet by
   (b) a pair of spaced electrically conductive tapes, coated with an electrically conductive adhesive coating, acting as two terminals of said pair of electrodes, to which a signalling means contained in a housing with a pair of conductive contacts on the housing can be attached in such a way that each one of said pair of tapes is electrically connected to a respective one of said pair of contacts when said diaper is in use; and
   (c) a backing sheet coated with an anti-adhesive coating normally covering said pair of conductive tapes, said backing sheet being adapted to be peeled off in order to allow adherence of said signalling means to said tapes when said diaper is to be used with said signalling means.

2. A disposable diaper set forth in claim 1 wherein: said signalling means is adapted to generate an audio sound when said diaper is wet.

3. A disposable diaper set forth in claim 1 wherein: a supporting sheet, coated with an adhesive coating on an inner side thereof, a portion of said supporting sheet adhering to the outer surface of said outer sheet and another portion of said supporting sheet adhering to said backing sheet, is adapted to hold said signalling means more tightly to said diaper when said signalling means is in use with said diaper.

4. A disposable diaper set forth in claim 3 wherein: said signalling means is adapted to generate an audio sound when said diaper is wet.

5. A means for detecting and signalling the presence of urine or fecal matter comprising in combination:
   (a) a disposable diaper having an inner sheet, an absorbing sheet, and an outer sheet, and also including:
      (1) a pair of spaced electrodes embedded longitudinally in a major part of said diaper with one of the ends of each of said electrodes extending out through a respective one of two apertures on said outer sheet terminated on the outer surface of said outer sheet by
      (2) a pair of spaced electrically conductive tapes, coated with an electrically conductive adhesive coating, acting as two terminals of said pair of electrodes, to which a signalling means contained in a housing with a pair of spaced conductive contacts on the housing can be attached in such a way that each one of said pair of tapes is electrically connected to a respective one of said pair of contacts when said diaper is in use; and
      (3) a backing sheet coated with an anti-adhesive coating normally covering said pair of conductive tapes, said backing sheet being adapted to be peeled off in order to allow adherence of said signalling means to said tapes when said diaper is to be used with said signalling means;
   (b) a signalling device consisting of:
      (1) a button type battery;
      (2) a CMOS voltage comparator with a reference voltage set by a Zener diode and a first resistor powered by said battery;
      (3) a beeper containing an oscillating means and a driving means with one end of said beeper connected to said battery and another end of said beeper connected to the output of said voltage comparator;
      (4) a voltage divider, connected across said battery, comprising a second resistor and a pair of conductive wires for measuring resistance across the said pair of electrodes embedded in the said diaper, one of said pair of conductive wires being connected with said second resistor and also being connected with the input of said voltage comparator; and
      (5) said housing comprising a top part and a bottom part with said pair of spaced conductive contacts on an outer face of said bottom part, each one of said pair of conductive contacts being electrically connected to a respective one of said pair of conductive wires.

6. A means for detecting and signalling the presence of urine or fecal matter set forth in claim 5 wherein: a supporting sheet, coated with an adhesive coating on an inner side thereof, a portion of said supporting sheet adhering to the outer surface of said outer sheet and another portion of said supporting sheet adhering to said backing sheet, is adapted to hold said device more tightly to said diaper when said device is in use with said diaper.

7. A means for detecting and signalling the presence of urine or fecal matter set forth in claim 5 wherein:
said pair of contacts are set into recesses on the outer face of said bottom part of said housing, for the purpose of measuring resistance across said pair of electrodes embedded in said diaper.

8. A means for detecting and signalling the presence of urine or fecal matter set forth in claim 5 wherein:
said top part and said bottom part of said housing are made in such a way that they can be snapped together and said top part of said housing has an opening for releasing alarm sound.

9. A means for detecting and signalling the presence of urine or fecal matter set forth in claim 5 wherein:
the value of said second resistor is chosen in such a way that when said pair of electrodes embedded in said diaper is bridged by urine or fecal matter, the voltage on said input of said comparator is less than said reference voltage of said comparator, and said output of said comparator goes low, therefore turning on said beeper; and when said pair of electrodes embedded in said diaper is bridged by dry diaper, the voltage on said input of said comparator is greater than said reference voltage said comparator, and said output of said comparator stays high, therefore allowing said beeper to remain off.

* * * * *